(12) United States Patent
Fisher et al.

(10) Patent No.: US 6,827,443 B2
(45) Date of Patent: Dec. 7, 2004

(54) METHOD AND SYSTEM FOR PRESCRIBING AND/OR DISPENSING OPHTHALMIC LENSES

(75) Inventors: Scott Warren Fisher, Flagstaff Hill (AU); John Charles Bonnett, Panorama (AU); David Robert Pope, Rohnert Park, CA (US)

(73) Assignee: Sola International Holdings, Ltd., Lonsdale (AU)

(*) Notice: Subject to any disclaimer, the term of this patent is extended or adjusted under 35 U.S.C. 154(b) by 91 days.

(21) Appl. No.: 10/181,988

(22) PCT Filed: Feb. 23, 2001

(86) PCT No.: PCT/AU01/00198

§ 371 (c)(1),
(2), (4) Date: Oct. 9, 2002

(87) PCT Pub. No.: WO01/62139

PCT Pub. Date: Aug. 30, 2001

(65) Prior Publication Data

US 2003/0107707 A1 Jun. 12, 2003

(30) Foreign Application Priority Data

Feb. 25, 2000 (AU) .............................................. PQ5918

(51) Int. Cl.[7] .............................. A61B 3/14; A61B 3/00
(52) U.S. Cl. ....................................... 351/209; 351/246
(58) Field of Search ................................ 351/200, 205, 351/209, 210, 246, 41, 159, 177; 128/898

(56) References Cited

U.S. PATENT DOCUMENTS

| | | | |
|---|---|---|---|
| 3,737,217 A | | 6/1973 | Haines et al. |
| 4,656,590 A | | 4/1987 | Ace |
| 4,856,891 A | * | 8/1989 | Pflibsen et al. ............. 351/210 |
| 4,961,640 A | * | 10/1990 | Irlen ............................ 351/44 |
| 5,329,322 A | * | 7/1994 | Yancey ........................ 351/211 |
| 5,345,281 A | | 9/1994 | Taboada et al. |
| 5,777,719 A | * | 7/1998 | Williams et al. ............. 351/212 |
| 6,027,216 A | * | 2/2000 | Guyton et al. .............. 351/200 |
| 6,090,051 A | * | 7/2000 | Marshall ...................... 600/558 |

FOREIGN PATENT DOCUMENTS

| | | |
|---|---|---|
| GB | 2267159 | 11/1993 |
| JP | 10-113334 | 5/1998 |
| WO | WO 93/01744 | 2/1993 |
| WO | WO 95/31927 | 11/1995 |
| WO | WO 99/26525 | 6/1999 |

OTHER PUBLICATIONS

Žangemeister, W.H. et al., Types of Gaze Movement: Variable Interactions of Eye and Head Movements, 1982, Experimental Neurology 77, pp. 563–577.*

* cited by examiner

Primary Examiner—Brian L. Casler
Assistant Examiner—John R. Sanders
(74) Attorney, Agent, or Firm—Burns, Doane, Swecker & Mathis, LLP

(57) ABSTRACT

A system and method for prescribing and/or dispensing ophthalmic lenses for a wearer. The method includes determining at least the wearer's individual visual behavioural patterns in terms of head movement and/or eye movement, processing those patterns with respect to a predetermined relationship between known head movements and/or eye movement characteristics and available ophthalmic lenses, such that the processing categorises wearers into a head movement or eye movement category that can then be used to produce a recommendation for an ophthalmic lens for the wearer. The system includes a transmitter unit (10), receivers on the user (12, 14) providing data to the interface (16). During a test a standard set of frames (18) are used, as are near (20) and intermediate (22) distance reading planes.

32 Claims, 5 Drawing Sheets

METHOD AND SYSTEM FOR PRESCRIBING AND/OR DISPENSING OPHTHALMIC LENSES

FIELD OF THE INVENTION

The present invention relates to the prescription and/or dispensing of ophthalmic lenses, typically lenses for spectacles or sunglasses.

The prescribing and dispensing of ophthalmic lenses includes several discrete aspects. In general terms, the act of prescribing is the determination of a wearer's required refractive power, such as the determination of the wearer's requirements for near and/or intermediate addition power. Similarly in general terms, the act of dispensing usually includes not only the selection of a suitable lens design but also the selection of a suitable frame (both optically and aesthetically) and the physical act of fitting the frame to a wearer, and the lens design to the frame relative to the wearer's reference position.

The method and system of the present invention have been found to provide particular benefits when used for dispensing that involves the selection of a suitable lens design for an individual wearer. However, it is to be appreciated that the present invention is not to be limited to only this aspect of dispensing, nor only to dispensing per se. Indeed, and as will be described in more detail below, the method and system of the present invention may also find beneficial uses in other dispensing aspects (and also in aspects of prescription), and may for example be useful for the custom generation of ophthalmic lenses to suit individual wearer's needs.

BACKGROUND OF THE INVENTION

In the last 10 years, the design of ophthalmic lenses has advanced to a stage where there are now several different lens designs available for each category of lens type, such as for single vision lenses and progressive lenses. Referring particularly to progressive lenses, there is thus available to a dispenser a large number of progressive lens designs that may be dispensed to a wearer, each of which would be suitable to meet that wearer's prescription requirements.

However, it has been recognized that individual wearers have differing physical features (such as stature, physique and shape), and also have different visual behavioural patterns (such as head, eye and postural behaviour while reading). All of these differing elements thus result in different lens designs being suitable for different wearers.

It is believed that, to date, and particularly with the development of differing types of progressive lens designs, dispensers have typically only used intuitive reasoning for recommending one particular lens design over another. Alternatively, dispensers may simply have relied on the lens manufacturer's own information.

It is an aim of the present invention to provide a method and a system that can be used on-site by a dispenser, at least to provide a recommendation for the selection of a suitable lens design from a group of known lens designs, preferably in a reasonably short period of time.

SUMMARY OF THE INVENTION

The present invention provides a method for prescribing and/or dispensing ophthalmic lenses for a wearer, the method including determining at least the wearer's individual visual behavioural patterns, analysing the visual behavioural patterns to provide visual behavioural data for the wearer and manipulating the visual behavioural data to provide, a lens design recommendation suitable for use in providing the wearer with a suitable ophthalmic lens.

The manipulation of the wearer's visual behavioural data may include the comparison of that data with optical attributes of a group of standard ophthalmic lens designs, and the subsequent selection therefrom of a standard ophthalmic lens that is suitable for the wearer. Such a comparison will ideally be made with respect to a predetermined relationship between visual behavioural patterns and the standard ophthalmic lens designs. In this respect, reference to the term 'standard' is to be understood to be reference to an ophthalmic lens or ophthalmic lens design that is in accordance with standard specifications, and has not been custom manufactured to the requirements of an individual wearer.

Alternatively, the manipulation of the wearer's visual behavioural data may include the generation of a custom ophthalmic lens design, and the subsequent manufacture of a custom ophthalmic lens that is suitable for the wearer. The generation of such a custom ophthalmic lens design may or may not utilize predetermined relationships between the known visual behavioural data and standard ophthalmic lens designs.

The method of the present invention seeks to at least identify a wearer's typical head movement and/or typical eye movement, and preferably to utilise a relationship between head and/or eye movement characteristics and the wearer's suitability for a particular lens design. In a simple form of the invention that relates to the dispensing of progressive lenses, the method preferably relies on a relationship that categorises wearers as either predominantly head movers or predominantly eye movers, particularly during reading, in order to allow accurate selection of a suitable progressive lens.

In this simple form, a wearer who may be categorised as an eye mover may, for example, require a progressive lens that provides a wide range of clear vision in the near zone, as the eyes will generally rove across almost the full width of the near zone when reading. Indeed, an eye mover may possibly be a person who is not well suited to a progressive lens at all.

On the other hand, the eyes of a wearer who may be categorised as a head mover will generally only utilise the central portion of the near zone of a progressive lens (due to the compensating movement of the wearer's head when reading), thus allowing the use of a more traditional progressive lens with a narrower near zone. Such a person is generally considered to be well suited to the use of a progressive lens.

Additionally, similar categorisations may be used to assist with frame selection, particularly in terms of lens size. For example, some ophthalmic lenses are relatively small in order to be fitted into fashionable frames. However, if a wearer is categorised according to the method of the present invention as an eye mover, a relatively small lens may present that wearer with viewing difficulties when their eyes rove across the full extent of the lens, especially when their eyes use the peripheries of the lens where there may typically be greater distortion and blur or rove past the frame boundary.

By utilising the method of the present invention, a dispenser will be able to recommend that the wearer not use frames that require such small lenses, or alternatively may recommend a specific lens that has been designed to have minimum peripheral distortion and blur.

Therefore, not only would the method of the present invention find use for the dispensing of ophthalmic lenses, but also in research areas for the development of lens designs that can cater for different wearer's requirements in terms of them being predominantly head movers or predominantly eye movers.

Hence, the present invention also provides a method for prescribing and/or dispensing ophthalmic lenses for a wearer, the method including determining at least the wearer's individual visual behavioural patterns in terms of head movement and/or eye movement, processing those patterns with respect to a predetermined relationship between known head movement and/or eye movement characteristics and available ophthalmic lenses, such that the processing categorises wearers into a head movement or eye movement category that can then be used to produce a recommendation for an ophthalmic lens for the wearer.

Furthermore, and in terms of the present invention being embodied in suitable apparatus, the present invention additionally provides a system for prescribing and/or dispensing ophthalmic lenses for a wearer, the system including means for determining at least the wearer's individual visual behavioural patterns, means for analysing the visual behavioural patterns to provide visual behavioural data for the wearer and means for manipulating the visual behavioural data to provide a lens design recommendation suitable for use in providing the wearer with a suitable ophthalmic lens.

In this form of the invention, the means for determining at least the wearer's individual visual behavioural pattern further includes means for sensing the wearer's head position, means for formatting the wearer's sensed head position in the form of wearer's sensed head position data, means for storing the wearer's sensed head position data and means for processing the wearer's sensed head position data.

In yet another form of the invention, the means for determining the visual behavioural pattern further includes means for sensing the wearer's eye position, means for formatting the wearer's sensed eye position in the form of wearer's sensed eye position data, means for storing the wearer's sensed eye position data and means for processing the wearer's sensed eye position data.

Ideally, the means for sensing the wearer's head position and the means for formatting the wearer's sensed head position as head position data are provided by a single piece of equipment referred to as head tracking apparatus.

In an alternative form, the means for sensing the wearer's eye position and the means for formatting the wearer's sensed eye position as eye position data may be provided by a single piece of equipment referred to as eye tracking apparatus.

The present invention also provides a system for prescribing and/or dispensing ophthalmic lenses for a wearer, the system including means for determining at least the wearer's individual visual behavioural patterns in terms of head movement and/or eye movement, means for processing those patterns with respect to a predetermined relationship between known head movement and/or eye movement characteristics and available ophthalmic lenses, means for categorizing the wearer into a head and/or eye movement category and means for recommending an ophthalmic lens for the wearer corresponding to the wearer head and/or eye movement category.

It will thus be recognised that the method and system of the present invention aim to match a wearer to a lens design (and vice-versa), rather than to force a wearer to adapt to a lens design. In this respect, when a new lens is worn for the first time, or when a lens design is changed, or when a new lens design is introduced to the market, wearers have traditionally been forced to modify their visual behavioural patterns. This usually results in a difficult period of time for a wearer (particularly a wearer whose visual behavioural patterns are not well matched to the new lens design), which will often result in rejection of a particular lens type and possibly even failure of a new lens design on the market.

However, by utilising the method and system of the present invention, a dispenser can ensure that wearers are fitted with lens designs that suit the wearer's visual behavioural patterns, thus avoiding rejection of a new lens design simply because of an inappropriate matching of a lens design to a wearer, and also minimising any difficult introduction period. Indeed, the method and system of the present invention are capable of analyzing various of the physical, and/or optical and/or environmental characteristics of an individual wearer, and either relating those characteristics to known categories of lens designs, and subsequently recommending for the dispenser a suitable lens design selected from a group of known lens designs, or for making a custom lens design for an individual wearer, which custom lens design is based upon the analysis of the various characteristics.

GENERAL DESCRIPTION OF THE INVENTION

A wearer's individual visual behavioural patterns may be determined in any known way, although it is preferred to do so in a manner that at least produces data that may be used to determine whether a wearer can be categorised as a head mover or an eye mover when tested during near and intermediate viewing.

In one form, this may require use of a spacial motion tracking system that is capable of recording head position and reading material position information. From this information, both reading ergonomics (such as head tilt, head rotation, and reading material distance and angle) and eye movement data may be calculated. The data may then be displayed and analysed such that wearers can be categorised on the basis of at least head movement, eye movement and posture, which in turn can be used to recommend lens designs, lens product categories, frame/lens combinations, or lens prescription.

In a preferred form of the present invention, the recording of data, the processing, display and analysis of that data, and the provision of a subsequent recommendation, are all functions that are performed by a computer.

In this respect, the data to be gathered and recorded from a wearer may be quite varied, and will be somewhat dependent upon the expected use for any particular system that utilises the present invention. For example, while the method of the invention will most likely be required to take into account various optical characteristics of the wearer, such as the nature and type of a wearer's current lens design and prescription, and the wearer's prescription status (namely, myope, emmetrope or hyperope), together with the characteristics referred to above as visual behavioural patterns, other external factors may also be taken into account.

While the gathering and recordal of any external factors, as well as the optical characteristics mentioned above, will most likely be a simple matter of manual data entry, gathering and recordal of the visual behavioural patterns of a wearer will generally require more than that, and may require monitoring and/or measurement of the wearer to determine various elements, with subsequent analysis and calculation to determine further elements.

For example, the visual behavioural patterns that care preferably utilised in the method of the present invention will most usually be embodied in head movement and/or eye movement when a wearer views a subject (such as when reading). Whilst head movement may be relatively easy to detect and measure, eye movement typically will not be. Thus, in a preferred form of the present invention, characteristics of head movement and eye movement may be determined by measuring elements that can be referred to as visual ergonomics, such as wearer's head tilt, head rotation, and reading material distance and angle.

By gathering and recording such visual ergonomic data it is possible to calculate a wearer's eye movements. There should subsequently be sufficient information from which to determine if a wearer should be categorized as an eye mover or a head mover, if that is the categorisation required to achieve the dispenser's aim for the method of the present invention.

With regard to the relationships that assist in categorising wearers, it must be appreciated that these relationships are generally to be determined in accordance with the dispenser's aims for the method being used. For example, if the method of the present invention is being used to provide recommendations for particular progressive lens designs, then it is expected that the categorisation of wearers as head movers or eye movers will suffice. However, it will be appreciated that this will require a determination to have been made as to a degree of head movement and a degree of eye movement below or above which a wearer will be appropriately categorised.

For example, it may be acceptable to define low, medium and high amounts of head turn (in degrees) together with low, medium and high amounts of eye declination (in degrees) when a wearer is tested using a spacial motion tracking system as will be described below, by determining arbitrary cut-off values in accordance with statistical populations. Thus, the processing of the data gathered and recorded by such a spacial head tracking system may simply provide as an output the location of a wearer's visual behavioural patterns in a matrix such as in Table 1 below, where the five asterisks identify a sample location:

TABLE 1

|  |  | Head Turn | | |
|---|---|---|---|---|
|  |  | High | Medium | Low |
| Eye Declination | High |  |  |  |
|  | Medium |  | ***** |  |
|  | Low |  |  |  |

In this example, where the dispenser is aiming to match a wearer to known types of progressive lens designs, a relationship between the matrix of Table 1 and the available types of progressive lens designs will also need to have been predetermined. A sample product recommendation table may be as follows in Table 2:

TABLE 2

|  |  | Head Turn | | |
|---|---|---|---|---|
|  |  | High | Medium | Low |
| Eye Declination | High | Progressive Lens Type A | Progressive Lens Type B | Progressive Lens Type C |
|  | Medium | Progressive Lens Type D | Progressive Lens Type D | Progressive Lens Type C |
|  | Low | Progressive Lens Type B | Progressive Lens Type E | Single Vision Lens |

As will be appreciated, in this example, the dispenser would recommend to the wearer that progressive lens type D would best suit that wearer's visual behavioural patterns, suitably weighted with influence from any of the other external and environmental elements and optical characteristics mentioned above, as necessary. In this respect, such weighting will preferably be included in either the analysis of the data to result in placing the wearer in a particular location in Table 1, or possibly in the determination of the alignment of particular lens types to particular locations in the matrix of Table 2.

DESCRIPTION OF A PREFERRED EMBODIMENT OF THE INVENTION

The method and system of the present invention will now be described in relation to a preferred embodiment. It is thus to be appreciated that the following description is not to limit the generality of the above description. To assist in an understanding of the following description, various drawings will be referred to. In the drawings.

Figure 1:
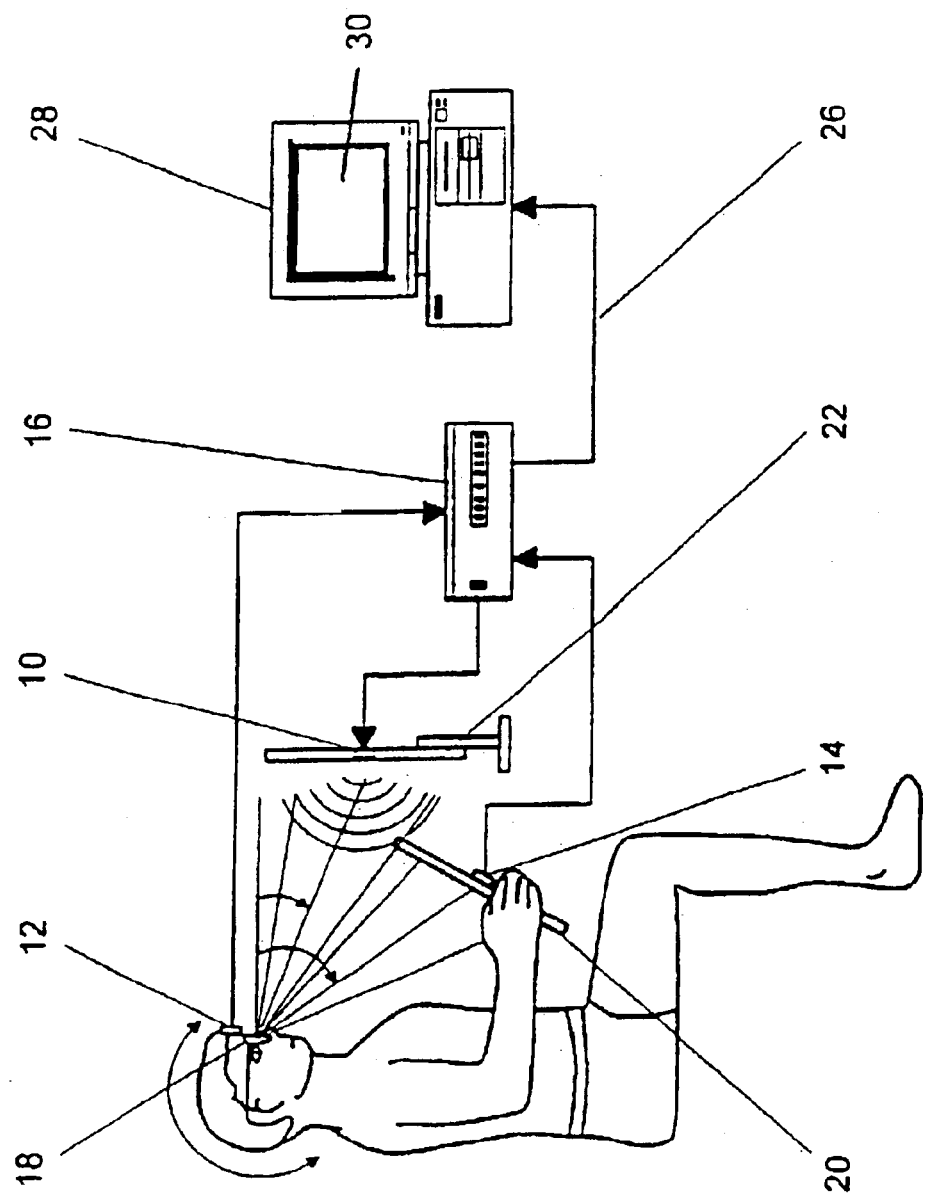
FIG. 1 is a simplified block diagram of a preferred embodiment of a head tracking system.
Figure 2:
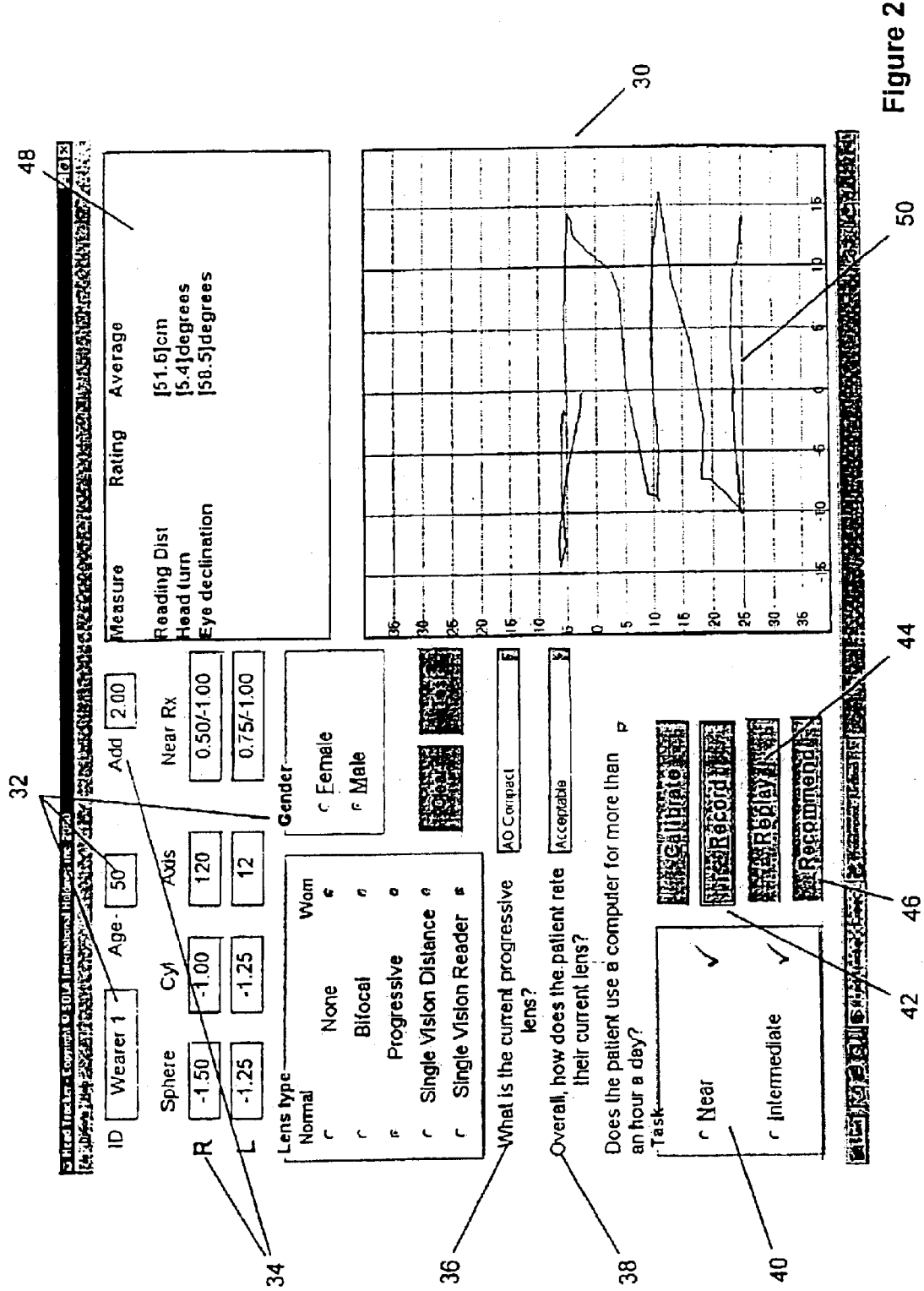
FIG. 2 is an illustration of a preferred layout of a graphical user interface that may be incorporated within the preferred embodiment of the present invention.

This preferred embodiment describes the use of a head tracking system that can be used in the method and system of the present invention for the dispensing and/or prescription of ophthalmic lenses. The main aim for the method and system of the preferred embodiment is thus to classify progressive lens wearers into progressive lens categories from which a particular progressive lens product can be dispensed.

In brief, the head tracking system records the wearer's head position and visual stimulus (reading material) position during a set of visual tasks which are performed by the wearer. Preferably, the set of visual tasks includes a near task and an intermediate task.

From the recorded head position and reading material position information, both visual ergonomics and eye movement data may be calculated, following which the data may be displayed and analysed such that the wearer can be categorised on the basis of head, eye and posture which is in turn used to recommend lens design, lens product categories, or frame and lens combinations. Preferably, the recommendation is presented in the form of a primary and a secondary recommendation wherein both recommendations comply with the wearer's progressive lens category but where each may differ on the basis of a parameter which is unrelated to the progressive lens category (for example, price).

In general terms, the head tracking system preferably includes the following components:

a. a wearer behavioural statistical model (database);
b. a matrix of progressive lens categories associated with the wearer behavioural statistical model;

c. head and reading material tracking hardware (herein referred to as the head tracking hardware);
d. a computer device including display, keyboard and mouse; and
e. customised application software.

With reference to the wearer behaviour statistical model, the model preferably consists of a population sample of head and eye measurements. Preferably, the model is used to generate summary statistics of head turn, eye turn, head declination and eye declination for the near task, and head turn and eye turn for the intermediate task. The summary statistics are used to identify values which define the low, medium and high characterisations for each of these variables.

Preferably, the values derived from the statistical analysis of the wearer behaviour statistical model are then used to define a set of classification ranges wherein each classification range is associated with a particular head and/or eye movement classification (for example, a high near eye declination classification range). The derived ranges may be incorporated into conditional tests within the customised application software, thus providing a mechanism for correlating empirical wearer visual behavioural parameters with a particular progressive addition lens category. The correlation between the empirical wearer visual behavioural parameters and a progressive addition lens category is presented in the form of a matrix, based on a predetermined relationship which will be described later.

The head tracking hardware used is preferably a multi channel motion sensing system that can simultaneously track the position and attitude of multiple targets (for example, the wearer's head and the reading material). One example of a suitable motion sensing system is a Polhemus 'Fastrack' system (schematically illustrated in FIG. 1) which consists of a transmitter 10, two receivers 12, 14 and an interface unit 16. When placed in the proximity of the transmitter 10 the receivers 12, 14 provide data which is interpreted by the interface unit 16 as the displacement between the transmitter 10 and the receivers 12, 14 in three dimensional space in terms of the orthogonal axes x, y and z, and angles according to azimuth, elevation and roll.

Attaching one of the receivers 12 to a wearer's head makes the system a head tracking device, with azimuth being equated to head turn, elevation to head declination and roll to head tip. This is achieved by mounting the first receiver 12 on a known type of ophthalmic lens trial-frame 18 to be worn by the wearer during the trial. The second receiver 14 is attached to a near task reading plane 20 to separately provide an indication of the near task reading distance and near task reading plane angle.

Pursuant to the preferred form of the present invention, the transmitter 10 is attached to an intermediate task reading plane 22.

During a trial, head position and reading material position are recorded while the wearer performs the set of visual tasks. For such a trial, and in order to control for frame and lens effects, all wearer's ideally use a standard trial-frame 18.

As indicated earlier, the set of visual tasks performed by the wearer includes a near task and an intermediate task. The near task consists of the wearer reading a particular arrangement of reading material on the near task reading plane 20. Preferably, the purpose of the near task is to derive results for near eye turn and near eye declination from the empirical near task head and reading positional information.

Pursuant to the preferred form of the invention, the reading material used for the near task consists of a page containing three paragraphs of approximately equal proportions (W×h). Preferably, each paragraph is positioned in one of three distinct zones where each zone is vertically separated by a blank segment having a vertical dimension which exceeds the vertical dimension (h) of each paragraph. The distribution of the zones is such that one paragraph is located on the top of the reading material separated from a second paragraph in the middle which is in turn separated from a third paragraph which is located towards the bottom of the reading material.

The intermediate task consists of the wearer reading a particular arrangement of reading material on the intermediate task reading plane 22. Preferably, the intermediate task reading material consists of a known geometric arrangement of characters in the form of a rectangular matrix, which is wider than it is high. Preferably, the arrangement of the matrix is such that the characters are uniformly spaced, both vertically and horizontally. Preferably, the purpose of the intermediate task is to derive a result for intermediate eye turn from the empirical intermediate task head and reading material positional information.

During a reading task, signals from the head tracking hardware receivers 10, 12 are monitored by the head tracking hardware interface unit 16 and are converted into a format suitable for transmission to a computer device via a communications link 26.

With reference now to the computer device and the customised application software, the customised application software executable code preferably resides on a peripheral storage device fitted to the computer device. In operation, the customised application software executable code is activated and "run" on the computer device. In this operational mode, the combination of the computer device and the customised application software is referred to as the programmed computer 28.

The programmed computer 28 preferably provides functions which enable head tracking hardware interface unit communications and the sampling, recording, gathering processing and analysis of head and reading material position raw data. In addition, the programmed computer 28 may also provide a graphical user interface (GUI) 30 which is operable by a system operator.

Pursuant to a preferred form of the invention, the GUI 30 provides a system operator with an interactive "windows" environment for entering the wearer's identification 32 and background data, and for controlling system functions. Preferably, the wearer's background data will include information in relation to the wearer's prescription (sphere, cylinder and addition) 34, a description 36 and subjective wearer assessment 38 of any existing progressive addition lens already used by the wearer and any other data considered relevant and useful.

Preferably, the GUI 30 provides interactive buttons and check boxes which are operable by the system operator to enable the selection of the desired reading task (near or intermediate) 40, recording control functions 42 and a recorded task replay function 44. Ideally, the GUI 30 will also includes controls which are enabled subject to a conditional test. For example, the GUI 30 may include a button 46 which is operable subsequent to the completion of the recording and processing of the near and intermediate tasks and which upon activation provides a primary and secondary recommendation for a lens type based on the recorded results.

The GUI 30 preferably also incorporates graphical windows for the display of summary results 48 and a graphical representation of head and reading material movements 50 during and subsequent to recording.

With particular reference to a preferred manner of sampling, recording, gathering and processing the wearer's head and reading material position raw data, subsequent to the enabling of the recording function, the programmed computer 28 will preferably periodically sample and record raw data received from the head tracking hardware interface unit 16 via the communications link 26. The relevance of the raw data will be dependant upon the reading task. For the near task, the raw data will generally consist of at least 6 measures of 6 degrees of motion for at least two reference planes, one on the wearer's head the other on the near reading target. For the intermediate task, generally only the raw data which consists of 6 measures of 6 degrees of motion for the wearer's head reference plane will be relevant for the case of a Polhemus 'Fastrack' system where the transmitter reference plane is attached to the intermediate reading plane.

In the preferred form of the invention, the programmed computer 28 processes near task data and intermediate task data according to the reading task.

For near task data, the programmed computer 28 will preferably store data received from the head tracking hardware in two arrays, one for each of the head and reading material receiver position, and orientation data at least consisting of sampled x, y and z in absolute three dimensional space and azimuth, pitch and roll of the reference plane.

The programmed computer 28 will preferably then filter the near task recorded data to exclude data not related to the reading task. The filtered data will preferably then be parsed to correlate segments of the filtered data with a particular paragraph of the near task reading material. Here, the programmed computer 28 utilises the wearer's head position and pitch data and reading material position and pitch data to compute a relative velocity of the wearer's projected line of sight relative to the near task reading material in the near task reading plane. High relative velocities, in the vicinity of the one third and two third sections of the filtered data are able to be interpreted by the programmed computer 28 as instants where the wearer traversed between the first and second and second and third paragraphs respectively. The programmed computer 28 preferably then partitions the filtered data into three data sets according to the identified high relative velocity boundary events whereby each set corresponds to a data record for a particular paragraph (i.e. upper, middle and lower paragraph data records).

The programmed computer 28 may then calculate a mean near task reading distance (the mean distance between the near task reading plane mounted receiver 14 and the head mounted receiver 12) and a maximum near task head rotation angle for each data record.

Preferably, the mean near task reading distance for each data record, is determined using a trigonometric calculation which includes the wearer's head mounted receiver position, the near task reading plane mounted receiver position and orientation, and the known geometry of the near task reading material. The mean near task reading distance calculation may also take into account a displacement between the wearer's eye position and the position of the head mounted receiver 12.

The programmed computer 28 preferably calculates the maximum near task head rotation angle for each data record using the standard deviation of the near task head turn (azimuth) data.

Subsequent to calculating the mean near task reading distance, the programmed computer 28 is able to compute, for each data record, a head rotation angle required for the wearer to reach the end of a paragraph line without an eye rotation.

The programmed computer 28 preferably then calculates, for each data record, an inferred near eye rotation as the difference between the maximum near task head rotation angle and the head rotation angle required for the wearer to reach the end of a line without an eye rotation.

The programmed computer 28 preferably then calculates the mean of the three near task data records inferred near eye rotation results which is then taken as the final near eye turn result.

Near eye declination may be determined based upon the wearer's head declination and the relative position, orientation and geometry of the near task reading material. Here, the programmed computer 28 is able to use the known geometric parameters of the near task reading material paragraphs, the measured position and orientation of the near task reading plane and the measured wearer's head declination to determine the angle (in the vertical plane) of each paragraph relative to the position of the wearer's head.

Subsequent to the calculation of the angle of each paragraph relative to the wearer's head, the programmed computer 28 may then estimate the relative near eye declination for each paragraph as the difference between the relative paragraph angle and the measured head declination.

Preferably, the programmed computer 28 calculates a mean near eye declination for each of the near task data records and derives a result from the set of mean results as a basis for the dispensing model.

With reference now to the processing of intermediate task data, only the head mounted receiver 12 position data is of relevance. Pursuant to the preferred form of the invention, the purpose of the intermediate task is to classify the wearer in terms of intermediate eye turn. Hence, only intermediate head turn data will be processed by the programmed computer 28. Furthermore, unlike the near task, the intermediate data will preferably not be parsed to establish a correlation between intermediate reading material targets and eye turn, nor is start and end data discarded.

Preferably, intermediate eye turn will be calculated using an approach which is similar to that used for the determination of near eye turn. That is, the maximum head rotation angle will be determined and then subtracted from the head rotation angle required for the wearer to view characters at the beginning and ends of the intermediate reading material lines without an eye rotation. The difference between these angles may then be interpreted as the inferred intermediate eye rotation.

Having described the principles underlying the processing of near task and intermediate task data, and the resultant derivation of the near and intermediate eye movement parameters, the step of associating the eye movement parameters with a particular progressive addition lens will now be described in detail.

Here, the results of the near and intermediate task data processing are combined with the wearer's background data and compared to the standard model derived classification range for each relevant parameter. Preferably, the comparison is implemented using a series of conditional tests incorporated within the application software (for example, case statements). The result of the comparison enables the position of a relevant parameter within a classification range to be determined, thereby classifying the wearer into a particular vision behavioural category. The programmed computer then, by using a predetermined relationship, selects a progressive addition lens which most closely matches the wearer's vision behavioural category.

With regard to such a predetermined relationship, and with particular reference to a relationship useful for a dispenser interested in progressive lens design choices, as with bi-focal lenses progressive lenses devote particular spatial locations on their surface to a particular viewing distance. Traditionally, the top of the progressive lens is for distance viewing while the bottom of the progressive lens is for near viewing, with a 'corridor' linking the two zones making a smooth transition between the zones. Unfortunately, it has not yet been possible to design a progressive surface without astigmatism or distortion flanking the viewing zones, although lens designers have been able to alter the viewing zone sizes and move the locations of the distortions around.

For example, some wearers complain that they have to tilt their head back too far in order to be able to read text up close. The solution is to shorten the length of the progression zone, namely the corridor length. Other patients object to having to move their head from side to side to read because the size of the near zone is not wide enough before they encounter distortions. In this situation, the lens designer can widen the near zone.

Clearly, if one can match the size, shape and location of the viewing zones of existing progressive lens designs to a wearer's typical eye movement patterns, as predicted on the basis of head and reading material movement or as directly measured with eye-tracking, a wearer will be more immediately satisfied. In the method and system of the present invention, progressive lens designs are preferably examined so as to match the zone locations and shapes as closely as possible to the expected patterns of usage of the lens surface.

Alternatively, other lens measures may be examined that may correlate with, or that are known to correlate with, wearer satisfaction, that may be predicted on the basis of head and reading stimulus movement. For example, wearers with large head movements may need designs that minimise motion distortions that may cause visually induced nausea or 'swim'.

Figure 3:
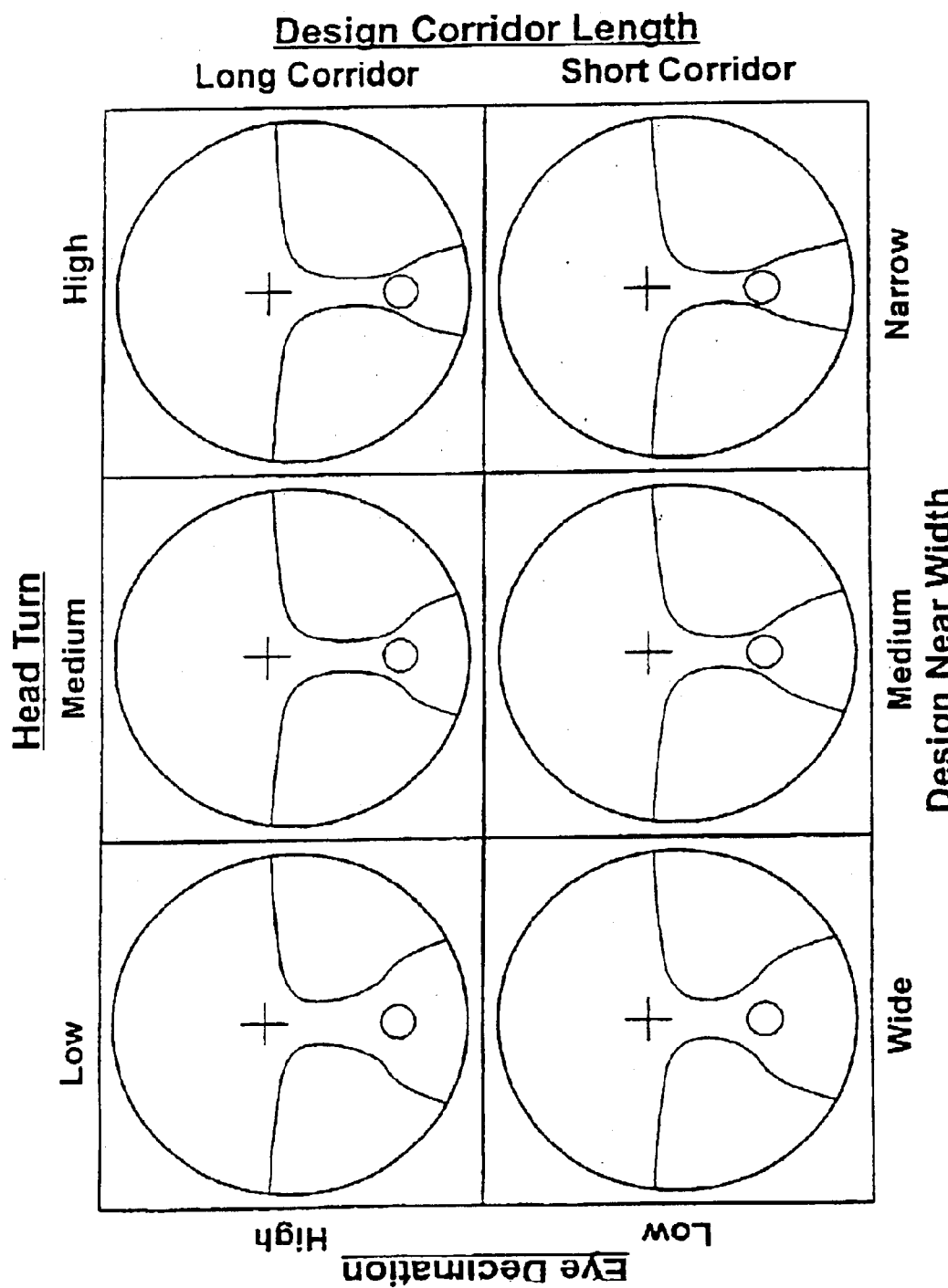
FIG. 3 is an example of a matrix used to associate a progressive addition lens type with a visual behavioural characteristic.
Figure 4:
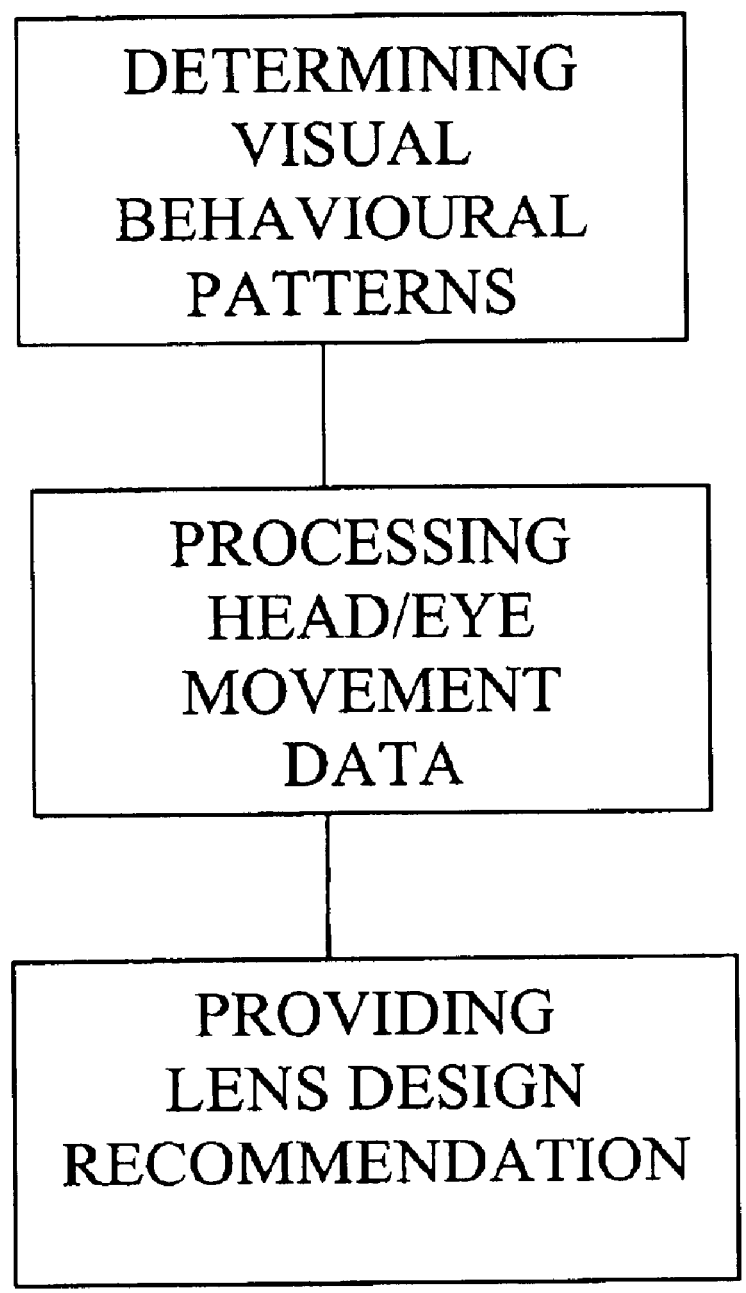
FIG. 4 is a flowchart showing the steps of a preferred method for prescribing and/or dispensing ophthalmic lenses for a wearer according to the present invention; and, FIG. 5 is a flowchart showing the steps of another preferred method for prescribing and/or dispensing ophthalmic lenses for a wearer according to the present invention.
Figure 5:
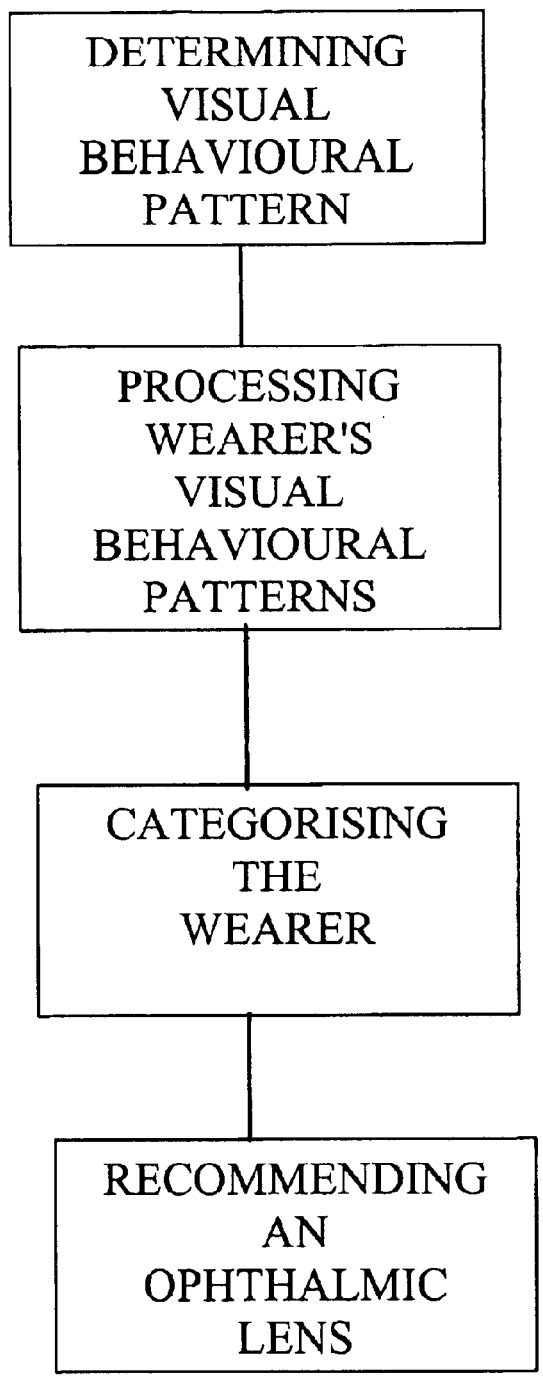

It is examining and matching of this type that assists in the generation of a suitable predetermined relationship in the method and system of the present invention. In this respect, a sample matrix that may be used as the predetermined relationship is illustrated in FIG. 3. FIG. 3 shows schematic lens plots of six progressive addition lenses (A to F). Each lens plot, bounded by a circle, has a cross representing the distance fitting point and a small circle representing the near power reference point. The curved lines flanking each lens represent the isoastigmatism contours that correspond to the limits of clear vision, or in other words represent the commencement of blur. Indeed, and as discussed above, astigmatism is often perceived by wearers as blur. These type of plots are used widely in the optical industry to compare lens designs.

The depicted designs vary systematically in two dimensions, namely in near zone width and corridor length. In relation to near zone width, the wider the separation between the isoastigmatism contours around the near reference circle, the larger the near zone area. In relation to corridor length, the further the distance between the distance and near reference points, the longer the corridor (ie, a wearer will have to rotate their eyes further down to reach the reading zone). Longer corridors generally afford lower peripheral astigmatism and distortion.

Specifically, design A has a long corridor and a wide near zone; design B has a long corridor and a medium width near zone; design C has a long corridor and a narrow near zone; design D has a short corridor and a wide near zone; design E has a short corridor and a medium width near zone; and design F has a short corridor and a narrow near zone.

With reference to these designs, a wearer who does not turn their head to read or rotate their eyes down would generally need a short corridor and a wide near zone, such as that in design D. On the other hand, a wearer who rotates their head a great deal while reading and rotates their eyes down would likely be satisfied with design C, thus taking advantage of the benefits associated not only with the more appropriate zone size and location but also the lower peripheral distortion.

With regard now to the preferred operation of the head tracking system, in the preferred method of the invention, a system operator will initially ensure that the system is ready for use by powering on the system and performing system built in test functions. Subsequent to passing the system built in tests, the system operator will enter the wearer's identification and background data into the system and then position the wearer in a suitable position with respect to the system. A trial-frame will then be fitted to the wearer's head, which trial-frame includes a receiver module and a pair of lenses in accordance with the wearer's prescription for the given reading task distance. Preferably, the trial-frame uses single vision lenses, however, other lens types could also be used.

The system operator will then request the wearer to adopt a head position whereby the wearer's line of sight is approximately parallel to the horizon. Furthermore, the system operator will ensure that the near task reading material is positioned flat on a desk or similar structure. The system operator will then enable a system calibration wherein positional information received from the head tracking hardware during the calibration step is decoded by the programmed computer and used to establish a set of reference coordinates.

The system operator will then prompt the wearer to pick up the near task reading material, if they wish to, and commence reading. Subsequent to the receipt of an aural cue from the wearer indicating the start of the near task the system operator will enable the system recording control which initiates recording. In an alternative embodiment, the start of the reading task may be sensed by the system and used to start the recording process automatically.

Head and reading material positional data will then be periodically sampled in 6 degrees of freedom and recorded for the duration of the near task by the programmed computer. During the recording process the system will provide the system operator with a graphical display of recorded head and reading material movements to provide an indication that the system is functioning correctly. The system operator will halt the recording process immediately following the receipt of a second aural cue from the wearer indicating completion of the near task. In an alternative embodiment, the completion of the reading task may be sensed by the system and used to halt the recording process automatically.

The system operator will then instruct the wearer to commence reading the intermediate task reading material. Once again, the system recording function is enabled and disabled by the system operator in response to aural cues from the wearer or automatically.

Subsequent to the completion of the near, intermediate and any other relevant tasks, the system operator then instructs the programmed computer to save the recorded data and provide a primary and secondary recommendation for a progressive addition lens based on the recorded data. The receipt of the request to recommend a progressive addition lens triggers the programmed computer to process and analyse near and intermediate data as well as the wearer's background data in accordance with the methodology presented earlier. The result of the processing and analysis is a primary and secondary recommendation for a progressive addition lens.

Finally, it will be understood that there may be other variations and modifications that may be made to the embodiments described herein that will also be within the scope of the present invention.

What is claimed is:

1. A method for prescribing and/or dispensing ophthalmic lenses for a wearer including:
   a. determining at least the wearer's individual visual behavioural patterns in terms of head movement and/or eye movement data;
   b. processing the head movement and/or eye movement data so as to categorise the wearer into a head and/or eye movement category; and
   c. providing a lens design recommendation for the wearer according to the wearer's head and/or eye movement category.

2. A method according to claim 1, wherein the providing of a lens design recommendation for the wearer according to the wearer's head and/or eye movement category includes selecting a standard ophthalmic lens design that has been matched with the wearer's head and/or eye movement category.

3. A method according to claim 2 wherein the selecting of a standard ophthalmic lens design that has been matched with the wearer's head and/or eye movement category includes selecting the standard lens from a Group of standard ophthalmic lens designs, each of the standard ophthalmic lens designs being matched with a different head and/or eye movement category.

4. A method according to claim 1 wherein the providing of the lens design recommendation for the wearer according to the wearer's head and/or eye movement category includes generating a custom ophthalmic lens design to be manufactured for the wearer.

5. A method for prescribing and/or dispensing ophthalmic lenses for a wearer, including:
   a. determining at least the wearer's individual visual behavioural patterns in terms of head movement and/or eye movement;
   b. processing the wearer's individual visual behavioural patterns with respect to a predetermined relationship between known head movement and/or eye movement characteristics and available ophthalmic lenses;
   c. categorizing the wearer into a head and/or eye movement category; and
   d. recommending an ophthalmic lens for the wearer in accordance with the wearer's head and/or eye movement category.

6. A method according to claim 5 wherein the wearer's head movement behavioural patterns are determined based upon empirical wearer head positional data.

7. A method according to claim 6 wherein the empirical head positional data is derived from head tracking apparatus.

8. A method according to claim 5 wherein the wearer's eye movement behavioural patterns are determined based upon empirical eye positional data.

9. A method according to claim 8 wherein the empirical eye positional data is derived from eye tracking apparatus.

10. A method according to claim 5 wherein the wearer's head movement behavioural patterns are expressed in terms of:
    a. near head declination;
    b. near head turn;
    c. intermediate head turn; and
    d. intermediate head declination.

11. A method according to claim 5 wherein the wearers eye movement behavioural patterns are determined based upon the wearer's head movement behavioural patterns.

12. A method according to claim 5 where wherein the wearer's eye movement behavioural patterns are expressed in terms of:
    a. near eye turn;
    b. near eye declination;
    c. intermediate eye turn; and
    d. intermediate eye declination.

13. A method according to claim 5 wherein wearers are categorised as either predominantly head movers or predominantly eye movers.

14. A method according to claim 5 wherein the method is performed by a programmed computer in combination with head tracking apparatus.

15. A method according to claim 5 wherein the method is performed by a programmed computer in combination with eye tracking apparatus.

16. A system for prescribing and/or dispensing ophthalmic lenses for a wearer, the system including:
    a. means for determining at least the wearer's individual visual behavioural patterns in terms of head movement and/or eye movement data;
    b. means for processing the head movement and/or eye movement data so as to categorise the wearer into a head and/or eye movement category; and
    c. means for providing a lens design recommendation for the wearer according to the wearer's head and/or eye movement category.

17. A system according to claim 16 wherein the means for determining at least the wearer's individual visual behavioural pattern further includes:
    a. means for sensing the wearer's head position;
    b. means for formatting the wearer's sensed head position in the form of the wearer's sensed head position data;
    c. means for storing the wearer's sensed head position data; and
    d. means for processing the wearer's sensed head position data.

18. A system according to claim 17 wherein the means for sensing the wearer s head position and formatting the wearer's sensed head position as head position data includes a head tracking apparatus.

19. A system according to claim 16 wherein the means for determining at least the wearer's individual visual behavioural pattern further includes:
    a. means for sensing the wearer's eye position;
    b. means for formatting the wearer's sensed eye position in the form of the wearer's sensed eye position data;
    c. means for storing the wearer's eye position data; and
    d. means for processing the wearer's sensed eye position data.

20. A system according to claim 19 wherein the means for sensing the wearer's eye position and formatting the wearer's sensed eye position as eye position data includes a an eye tracking apparatus.

21. A system for prescribing and/or dispensing ophthalmic lenses for a wearer, the system including:
    a. means for determining at least the wearer's individual visual behavioural patterns in terms of head movement and/or eye movement;

b. means for processing those patterns with respect to a predetermined relationship between known head movement and/or eye movement characteristics and available ophthalmic lenses;

c. means for categorizing the wearer into a head and/or eye movement category; and d. means for recommending an ophthalmic lens for the wearer corresponding to the wearer's head and/or eye movement category.

22. A system according to claim 21 wherein the means for determining at least the wearer's individual visual behavioural patterns in terms of head and eye movement includes a programmed computer device in combination with head tracking apparatus.

23. A system according to claim 21 wherein the means for determining at least the wearer's individual visual behavioural patterns in terms of eye movement includes a programmed computer device in combination with eye tracking apparatus.

24. A system according to claim 21 wherein the means for processing at least the wearer's individual visual behavioural patterns with respect to a predetermined relationship between known head movement and/or eye movement characteristics and available ophthalmic lenses includes a programmed computer.

25. A system according to claim 21 wherein the means for categorizing the wearer into a head and/or eye movement category includes a programmed computer in combination with a wearer behavioural statistical model.

26. A system according to claim 21 wherein the means for recommending an ophthalmic lens for the wearer corresponding to the wearer's head and/or eye movement category is performed by a programmed computer in combination with a matrix of progressive lens categories associated with a wearer behavioural statistical model.

27. A method according to claim 1 wherein the lens design recommendation is a recommendation for a progressive addition lens design.

28. A method according to claim 16 wherein the lens design recommendation is a recommendation for a progressive addition lens design.

29. A method for prescribing and/or dispensing ophthalmic lenses for a wearer, including:

a. determining at least the wearer's individual visual behavioural patterns in terms of head movement and/or eye movement;

b. processing the wearer's individual visual behavioural patterns with respect to a predetermined relationship between known head movement and/or eye movement characteristics and a group of ophthalmic lenses, each of the ophthalmic lenses being matched to a head and/or eye movement category;

c. categorising the wearer into a head and/or eye movement category; and d. recommending an ophthalmic lens for the wearer, the recommended ophthalmic lens being matched to the wearer's head and/or eye movement category, the recommended ophthalmic lens being from the group of ophthalmic lenses.

30. A method according to claim 29 wherein each ophthalmic lens is a progressive addition lens.

31. A system for prescribing and/or dispensing ophthalmic lenses for a wearer, the system including:

a. means for determining at least the wearer's individual visual behavioural patterns in terms of head movement and/or eye movement;

b. means for processing those patterns with respect to a predetermined relationship between known head movement and/or eye movement characteristics and a group of ophthalmic lenses, each of the ophthalmic lenses being matched to a head and/or eye movement category;

c. means for categorising the wearer into a head and/or eye movement category; and d. means for recommending an ophthalmic lens for the wearer, the recommended ophthalmic lens being matched to the wearer's head and/or eye movement category, the recommended ophthalmic lens being from the group of ophthalmic lenses.

32. A system according to claim 31 wherein each ophthalmic lens is a progressive addition lens.

* * * * *

UNITED STATES PATENT AND TRADEMARK OFFICE
CERTIFICATE OF CORRECTION

| | | |
|---|---|---|
| PATENT NO. | : 6,827,443 B2 | Page 1 of 1 |
| APPLICATION NO. | : 10/181988 | |
| DATED | : December 7, 2004 | |
| INVENTOR(S) | : Scott Warren Fisher et al. | |

It is certified that error appears in the above-identified patent and that said Letters Patent is hereby corrected as shown below:

Claim 28, Column 15, Line 40: change "method" to --system--.

Signed and Sealed this
Fourth Day of December, 2012

David J. Kappos
*Director of the United States Patent and Trademark Office*